(12) United States Patent
Johnson et al.

(10) Patent No.: US 10,758,739 B2
(45) Date of Patent: Sep. 1, 2020

(54) RESTRUCTURING NEURAL PATHWAYS IN THE BRAIN WITH A COMBINATION OF TRANSCRANIAL THERAPIES

(71) Applicant: MULTI RADIANCE MEDICAL, Solon, OH (US)

(72) Inventors: Douglas Johnson, Brownstown, MI (US); Max Kanarsky, Solon, OH (US)

(73) Assignee: MULTI RADIANCE MEDICAL, Solon, OH (US)

( * ) Notice: Subject to any disclaimer, the term of this patent is extended or adjusted under 35 U.S.C. 154(b) by 0 days.

(21) Appl. No.: 16/613,545

(22) PCT Filed: May 18, 2018

(86) PCT No.: PCT/US2018/033415
§ 371 (c)(1),
(2) Date: Nov. 14, 2019

(87) PCT Pub. No.: WO2018/213722
PCT Pub. Date: Nov. 22, 2018

(65) Prior Publication Data
US 2020/0069959 A1 Mar. 5, 2020

Related U.S. Application Data

(60) Provisional application No. 62/508,003, filed on May 18, 2017.

(51) Int. Cl.
*A61N 1/00* (2006.01)
*A61N 2/00* (2006.01)
(Continued)

(52) U.S. Cl.
CPC .......... *A61N 2/002* (2013.01); *A61B 5/04001* (2013.01); *A61B 5/0478* (2013.01);
(Continued)

(58) Field of Classification Search
CPC .... A61N 2/002; A61N 5/0622; A61N 5/0618; A61N 2/06; A61N 2/006; A61N 1/36025;
(Continued)

(56) References Cited

U.S. PATENT DOCUMENTS

| 9,456,784 B2 | 10/2016 | Helekar |
| 2009/0082690 A1 | 3/2009 | Phillips |

(Continued)

FOREIGN PATENT DOCUMENTS

| WO | 2011146777 A2 | 11/2011 |
| WO | 2012024243 A1 | 2/2012 |
| WO | 2016023126 A1 | 8/2016 |

OTHER PUBLICATIONS

International Search Report and Written Opinion dated Sep. 6, 2018 for Application No. PCT/US2018/033415.

*Primary Examiner* — Scott M. Getzow
(74) *Attorney, Agent, or Firm* — Tarolli, Sundheim, Covell & Tummino LLP

(57) ABSTRACT

Brain dysfunction can be treated by restructuring neural pathways in the brain. A desired area in the brain to form a new neural pathway is selected. The area receives a sequential combination of (1) transcranial photobiomodulation therapy (PBMT) including a series of pulses having a frequency matched to a target brain wave and (2) another transcranial stimulation (e.g., transcranial direct current electrical stimulation and/or transcranial magnetic stimulation). The different stimulation mechanisms ensure that neuroplasticity occurs to restructure a neural pathway that is dysfunctional in nature to a new neural pathway that conducts normally.

15 Claims, 5 Drawing Sheets

(51) Int. Cl.
*A61B 5/04* (2006.01)
*A61B 5/0478* (2006.01)
*A61N 1/20* (2006.01)
*A61N 1/36* (2006.01)
*A61N 2/06* (2006.01)
*A61N 5/06* (2006.01)
*A61N 5/067* (2006.01)

(52) U.S. Cl.
CPC ........... *A61N 1/20* (2013.01); *A61N 1/36025* (2013.01); *A61N 2/006* (2013.01); *A61N 2/06* (2013.01); *A61N 5/0618* (2013.01); *A61N 5/0622* (2013.01); *A61N 2005/067* (2013.01); *A61N 2005/0629* (2013.01); *A61N 2005/0652* (2013.01); *A61N 2005/0659* (2013.01); *A61N 2005/0663* (2013.01)

(58) Field of Classification Search
CPC ............... A61N 1/20; A61N 2005/067; A61N 2005/0663; A61N 2005/0659; A61N 2005/0652; A61N 2005/0629; A61N 1/00; A61N 2005/0662; A61B 5/0478; A61B 5/04001; A61B 5/4094; A61B 5/4088; A61B 5/04004; A61B 5/4064
See application file for complete search history.

(56) References Cited

U.S. PATENT DOCUMENTS

| 2014/0074176 | A1* | 3/2014 | Jansen ................. A61N 5/0622 607/3 |
| 2015/0119689 | A1 | 4/2015 | Pascual-Leone |
| 2016/0184603 | A1* | 6/2016 | Gilbert .................. A61K 33/00 604/20 |
| 2016/0220850 | A1 | 8/2016 | Tyler |
| 2016/0235980 | A1 | 8/2016 | Berman |
| 2016/0235983 | A1* | 8/2016 | Berman .................... A61N 1/40 |
| 2017/0096659 | A1 | 4/2017 | Ghosh |

* cited by examiner

RESTRUCTURING NEURAL PATHWAYS IN THE BRAIN WITH A COMBINATION OF TRANSCRANIAL THERAPIES

CROSS-REFERENCE TO RELATED APPLICATIONS

This application is a national stage entry of PCT Appl. No. PCT/US18/33415, filed May 18, 2019, entitled "RESTRUCTURING NEURAL PATHWAYS IN THE BRAIN WITH A COMBINATION OF TRANSCRANIAL THERAPIES", which claims the benefit of U.S. Provisional Application No. 62/508,003, filed May 18, 2017. This provisional application is hereby incorporated by reference in its entirety for all purposes.

TECHNICAL FIELD

The present disclosure relates generally to treating brain dysfunction and, more specifically, to systems and methods that restructure a neural pathway in the brain to treat brain dysfunction by applying a combination of transcranial therapies to an area of the brain.

BACKGROUND

The brain functions as the primary receiver, organizer, and distributor of information in the nervous system. To accomplish these tasks, the brain is made up of a complex network of neurons. Signals are transmitted between neurons via specialized connections called synapses. In the first few years of life, a child's brain can have as many as 15,000 synapses per neuron; however, the brain of the average adult has far fewer synapses per neuron. This is due to neuroplasticity, where some synapses are strengthened and others are eliminated over time due to the presence or absence of adequate stimulation. Neuroplasticity can occur as a result of learning, experience, and memory function, but may also occur as a result of damage to the brain. Such instances of neuroplasticity are often seen as improvements. However, neuroplasticity does not always cause positive changes; sometimes, these neuroplastic changes can lead to detrimental effects on the brain and behavior, such as misperceptions, pain, maladaptive behavior, or other indications of brain dysfunction.

SUMMARY

The present disclosure relates generally to treating brain dysfunction and, more specifically, to systems and methods that restructure a neural pathway in the brain to treat brain dysfunction by applying a combination of transcranial therapies to an area of the brain. The transcranial therapies can include photobiomodulation therapy (PBMT) and transcranial stimulation (e.g., transcranial direct current electrical stimulation (tDCS), transcranial magnetic stimulation (tMS), etc.).

In one aspect, the present disclosure can include a method for restructuring a neural pathway in the brain. A transcranial stimulation can be delivered at an intensity and for a time to an area of a brain of a patient requiring stimulation. The area of the brain corresponds to a desired neural pathway. A light signal can be delivered in a transcranial manner to the area of the brain for a second time. The light signal comprises a series of pulses having a frequency matched to a target brain wave. The brain undergoes neuroplasticity to form the desired neural pathway in response to the transcranial stimulation and the light signal.

In another aspect, the present disclosure can include a system that restructures a neural pathway in the brain. A transcranial stimulation mechanism can deliver a transcranial stimulation at an intensity and for a time to an area of a brain of a patient requiring stimulation. The area of the brain corresponds to a desired neural pathway. A light source can deliver a light signal in a transcranial manner to the area of the brain for a second time. The light signal includes a series of pulses having a frequency matched to a target brain wave. A processing unit can be preprogrammed to apply the transcranial stimulation for the time in sequence with the light signal for the second time. A power source can provide power to at least the processing unit.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
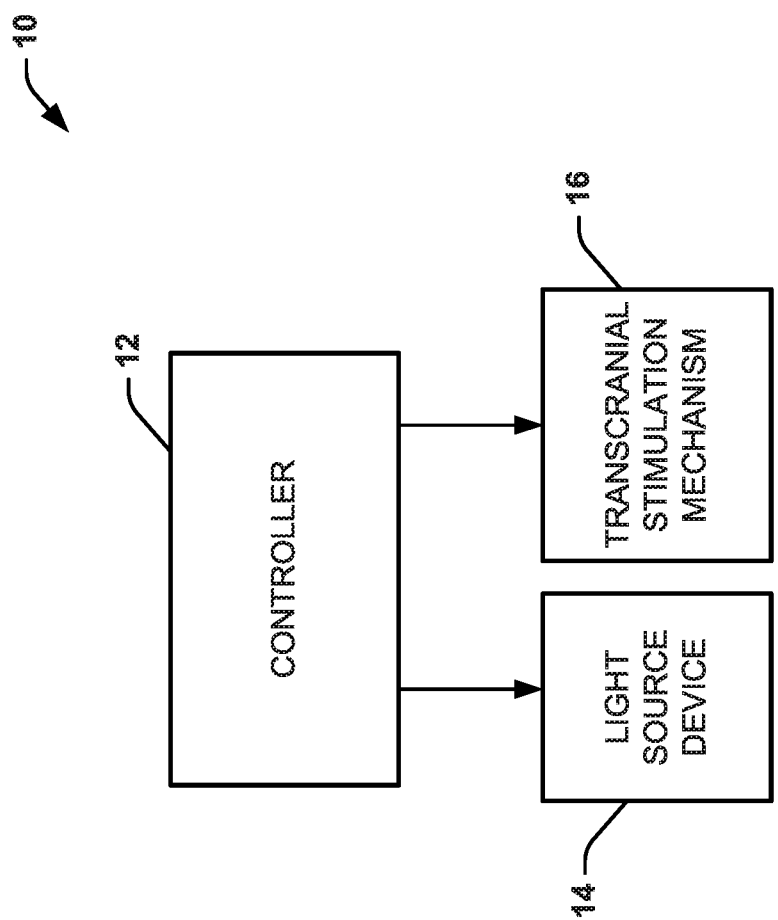
FIG. 1 is a block diagram illustration showing an example of a system that restructures a neural pathway in the brain in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the term "brain dysfunction" refers to a pathological manifestation in all or part of the brain, which is associated with, or caused by, mitochondrial dysfunction in all or part of the brain. Brain dysfunction can be characterized by one or more neural pathways that are abnormal in nature. Examples of brain dysfunction include mental illnesses (e.g., anxiety, depression, etc.), autism, Alzheimer's disease, epilepsy, traumatic brain injury, and the like.

As used herein, the terms "neural activity", "brain activity", and "activity" refer to the brain's spontaneous electrical activity (or "brain waves") over a period of time. Neural activity can be recorded using electroencephalography (EEG), which measures voltage fluctuations resulting from ionic current within the neurons of the brain. Multiple electrodes placed on the scalp can be used to record EEG data, which can be analyzed to show areas of high activity in the brain and areas of low activity in the brain.

As used herein, the term "brain wave" refers to voltage fluctuations resulting from ionic current within the neurons of the brain. When brain waves are out of balance (e.g., hyperactivity), brain dysfunction can occur. Brain waves can include, for example, infra-low brainwaves with a frequency less than 0.5 Hz, delta waves with a frequency of 0.5-3 Hz, theta waves with a frequency of 3-8 Hz, alpha waves with a frequency of 8-12 Hz, beta waves with a frequency of 12-38 Hz, gamma waves with a frequency of 38-42 Hz. The frequency of a light signal can be matched to the frequency of one or more brain waves.

As used herein, the term "neural pathway" refers to a series of nerve cells (or "neurons") connected together to enable a signal to be sent from one brain region to another.

As used herein, the term "neuroplasticity" refers to the brain's ability to reorganize itself by forming new neural connections throughout life. Neuroplasticity can allow neurons in the brain to compensate for injury or disease and to adjust their activities in response to new situations or to changes in environment.

As used herein, the term "transcranial" refers to something being done across or through the skull. Accordingly, a "transcranial therapy" refers to a therapy being performed across or through the skill. Examples of transcranial therapies can include transcranial photobiomodulation therapy, transcranial stimulation, and the like.

As used herein, the term "photobiomodulation" refers to the application of a light signal to a portion of a subject's body to induce a phototherapeutic response in cells within the portion of the subject's body.

As used herein, the term "photobiomodulation therapy (PBMT)" refers to a drug-free, non-invasive treatment procedure, in which a light signal is applied to a certain region of a subject's brain to treat a certain medical condition (e.g., brain dysfunction).

As used herein, the term "light signal" refers to light having at least one wavelength. However, the light signal may include a combination of lights having wavelengths that create a synergistic effect when combined and improves the percentage of available light at greater tissue depths. In some instances, the wavelengths can be within a wavelength range of 600-1100 nm. For example, the wavelengths can include at least one wavelength corresponding to the visible range of the electromagnetic spectrum (e.g., red light) and at least one wavelength corresponding to the near-infrared or infrared range of the electromagnetic spectrum.

As used herein, the term "light source device" refers to a mechanical implement that can deliver a light signal of PMBT transcranially to an area of a subject's brain.

As used herein, the term "light source" refers to a component of a light source device that delivers one or more lights of different wavelengths. For example, the light source can be a low-level laser source (e.g., a laser light emitting diode (LED)) that generates coherent light. The low-level laser source can operate in a super pulsed mode that generates ultrashort pulses with a high peak power and minimal heat. As another example, the light source can be an incoherent light source, such as a traditional LED or light bulb. The incoherent light source can operate in a pulsed mode and/or a continuous mode.

As used herein, the term "transcranial stimulation" refers to a drug-free, non-invasive treatment procedure, in which electricity is applied to a certain area of a subject's brain to treat a certain medical condition (e.g., brain dysfunction). Examples of transcranial stimulation can include transcranial direct current electrical stimulation (tDCS) (which delivers electricity), transcranial magnetic stimulation (tMS) (which induces the electricity), and the like.

As used herein, the term "proximal" refers to a location that is near a target. For example, a device that is located proximal an area in the brain can be located over the area in the brain, but need not be directly over the center of the area in the brain.

As used herein, the term "sufficient" refers to an amount adequate enough to satisfy a condition. For example, "a time sufficient to stimulate a phototherapeutic response in dystrophic muscle or muscle group" can refer to a light signal being applied to a dystrophic muscle or muscle group for a time adequate enough to stimulate the phototherapeutic response.

As used herein, the term "sequentially" can refer to following a particular order.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates to treating brain dysfunction. Previously, treatments for brain dysfunction have included the individual application of transcranial photobiomodulation therapy (PBMT) or transcranial stimulation (transcranial direct current electrical stimulation (tDCS), transcranial magnetic stimulation (tMS), or the like). While these treatments have been shown to provide temporary relief from the brain dysfunction, none of these treatments provides a solution for the brain dysfunction. The relief is only temporary with these treatments because these treatments do not truly restructure the neural pathway away from a dysfunctional area.

The present disclosure relates, more specifically, to systems and methods that restructure the neural pathway away from the dysfunctional area by promoting neural plasticity. For example, neural plasticity can involve deactivating the neural pathway that includes the dysfunctional area (or area of high neural activity), and activating a normal area (or area of low neural activity) to redirect the neural pathway. The activation can be accomplished by applying a combination of (1) transcranial photobiomodulation therapy (PBMT) and (2) transcranial stimulation (transcranial direct current electrical stimulation (tDCS), transcranial magnetic stimulation (tMS), or the like) to the area of low activity in the brain according to a specific dosage. While not wishing to be bound by theory, it is believed that the transcranial PBMT powers a metabolic process in mitochondria required for the activation of the area of low activity, increasing blood flow to the area of low activity in response to the metabolic demand, while the transcranial stimulation drives the stimulation of the area of low activity.

III. Transcranial Photobiomodulation Therapy (PBMT)

Using transcranial PBMT in combination with the transcranial stimulation can provide a solution for treating brain dysfunction by restructuring neural pathways away from a dysfunctional area. The neural pathway can be restructured away from a dysfunctional area of the brain to a preselected area of low activity. The transcranial stimulation can be applied to the area of low activity to drive the stimulation of the area of low activity. The transcranial PBMT can be applied to the area of low activity to reinforce the stimulation. The transcranial stimulation in combination with the transcranial PBMT can induce neural plasticity that can allow the restructuring of the neural pathway.

The light signal used for the transcranial PBMT has one or more wavelengths in the red to near infrared portion of the spectrum (600 nm-1100 nm) at a power density between 1 $W/cm^2$ and 5 $W/cm^2$. Transcranial PBMT exposes the area of low activity to a low-power, high-fluency source of monochromatic photon radiation, delivering energy doses that are too low to cause damage, yet high enough to modulate neuronal functions. The light signal can include pulses that are selected at a certain frequency equivalent to that of a target brain wave (e.g., 0 Hz-80 Hz depending on the target brain wave).

The neuro-modulatory action of red to near-infrared light wavelengths is based on the principle that certain molecules in living systems absorb photons and trigger signalling pathways in response to light. When a photon of light is absorbed by a chromophore in a cell, an electron in the chromophore can become excited and jump from a low-energy orbit to a higher-energy orbit. This stored energy then can be used by the system to perform various cellular tasks. While not wishing to be bound by theory, there is strong evidence to suggest that one of the basic cellular tasks mechanisms of transcranial PBMT is the acceleration of electron transfer by electromagnetic radiation in the visible and near infrared region of the spectrum, via the modulation of cytochrome c-oxidase ("CCO") activity in the mitochondria of neural cells within the area of low activity.

CCO is the primary photo acceptor of red to near infrared light energy and is the enzyme responsible for catalysing oxygen consumption in cellular respiration and for the production of nitric oxide under hypoxic conditions. High-energy electrons are passed from electron carriers through a series of trans-membrane complexes (including CCO) to the final electron acceptor, generating a proton gradient that is used to produce ATP. The application of light directly results in ATP production and electron transport. In short, the application of PBMT can increase ATP production, down-regulate cellular respiration modulated by NO, and promotes the metabolism of oxygen, while increasing the production of reactive oxygen species (ROS).

Transcranial PBMT can operate with a light signal having a single wavelength in the red to near-infrared region of the spectrum. However, the use of such single wavelengths may not effectively modulate CCO activity since the single wavelength is limited by its specific absorption spectrum. The light signal used in some instances described herein has a combination of wavelengths in the red to near infrared region of the spectrum, which are used concurrently, providing an overlapping effect of peak activation, which accelerates CCO activity. Additionally, the time of CCO activation is prolonged across the entire therapeutic window by delivering much smaller doses across many wavelengths, rather than a single wavelength of a greater power. The multiple wavelengths at least enhance adenosine triphosphate (ATP) production, requiring less energy, and provide continual photodissociation of nitric oxide (NO).

IV. Systems

One aspect of the present disclosure can include a system 10 (FIG. 1) that restructures a neural pathway in the brain. The system 10 can restructure the neural pathway to treat brain dysfunction (e.g., caused by a neurodegenerative disease, such as mental illnesses (e.g., anxiety, depression, etc.), autism, Alzheimer's disease, epilepsy, traumatic brain injury, and the like) by applying a combination of transcranial therapies to an area of the brain. The combination of transcranial therapies work together to induce neural plasticity that can allow the restructuring of the neural pathway.

The area of the brain can include a pre-identified target area. The transcranial therapies can include transcranial stimulation, which drives the stimulation of the target area, and transcranial photobiomodulation therapy (PBMT), which reinforces the stimulation of the target area. Both the transcranial stimulation and the transcranial PBMT are necessary to induce neural plasticity. The target area can be identified based on pre-treatment electroencephalography (EEG) data that is acquired (e.g., by an 18-channel EEG recording device) before treatment with the system 10. For example, high and low activity areas of the brain can be identified based on the EEG data, For example, the high and low activity areas can be identified based on conduction patterns seen in the EEG data (the high activity area of the brain can indicate brain circuit asymmetry). The high activity area can exhibit hyperactivity causing the brain dysfunction associated with the neurological disorder. The low activity area of the brain does not exhibit hyperactivity, so that the low activity area of the brain is not exhibiting the dysfunction. For example, the high activity area of the brain and the low activity area of the brain may be identified based on conduction patterns shown in the EEG data. The low activity area of the brain can be chosen as the target for the restructured neural pathway.

The system 10 can include a controller 12 that is connected to a light source device 14 and a transcranial stimulation mechanism 16. Although not illustrated in FIG. 1, the system 10 can also include a power source (e.g., internal battery and/or external power receiver/storage) to provide power to at least a portion of the controller 12 (e.g., a processing unit) and other electronics required for operation of the system 10.

Figure 2:
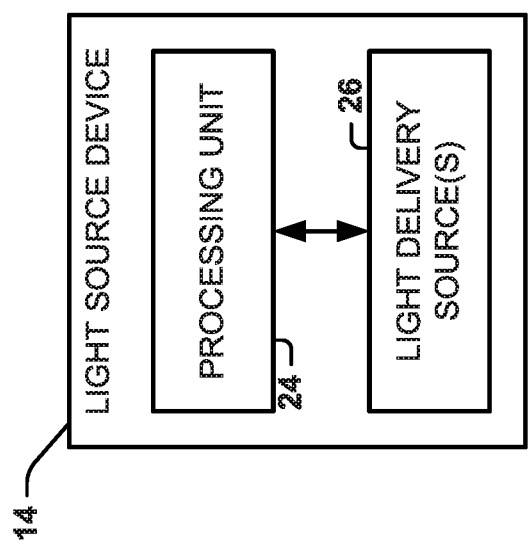
FIG. 2 is a block diagram illustration showing an example of the light source device of FIG. 1.

The light source device 14 can be configured to deliver a light signal associated with transcranial photobiomodulation therapy (PBMT) to the target area. An example of the light source device 14 is shown in FIG. 2 as including a processing unit 24 and one or more light delivery sources 26 to generate and provide the light signal. In some instances, the light signal can include a light wave at a single wavelength of light delivered in a certain operating mode. However, in other instances, the light signal can include a combination of a plurality of individual light waves with different wavelengths of light delivered in two or more different operating modes. The combination of individual light waves is advantageous because the individual light waves can work constructively to create a synergistic effect, enhancing each individual wavelength's ability to penetrate the skin, allowing for a greater portion of the available light energy to reach biological targets beneath the surface of the skin.

The plurality of individual light waves can be generated by a plurality of light delivery sources. Accordingly, the light source device 14 can include a plurality of light delivery sources, each configured to deliver light of a certain wavelength, with a given power, in a pulsed operating mode, a continuous operating mode, or a super-pulsed operating mode. One organization of the plurality of light delivery sources is in one or more light delivery source clusters 26 (an example of an individual cluster is shown in FIG. 2). In practice, the light source device can have any number of light delivery source clusters 26, limited only by the size of the area of the light source device 14 designated for delivery of the light signal.

Figure 3:
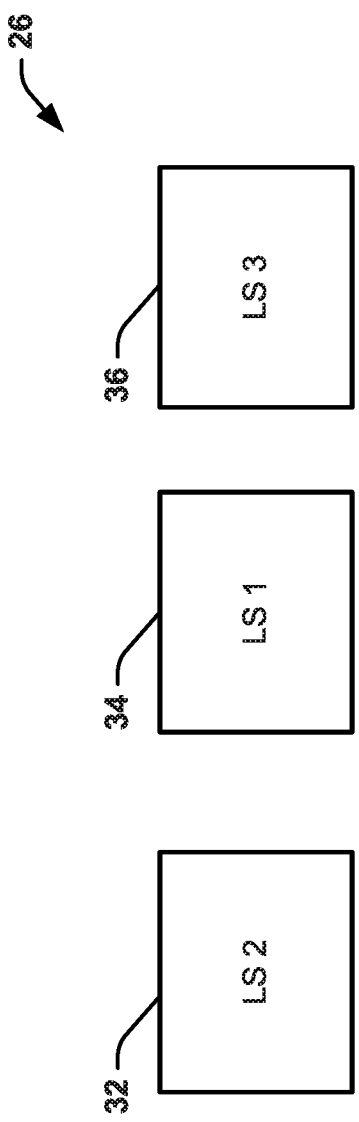
FIG. 3 is a block diagram illustration showing an example configuration of light sources within the light delivery source cluster of FIG. 2.

As shown in FIG. 3, each light delivery source cluster 26 includes three types of light sources (LS1 34, LS2 32, LS3 36). However, the light delivery source clusters 36 may include a greater or fewer number of light sources. Three light sources are shown for simplicity of illustration and explanation. The light sources (LS1 34, LS2 32, LS3 36) each generate light waves with wavelengths within a wavelength range of 600-1100 nm (red to infrared). More particularly, LS1 34 can be configured to generate a first portion of the light signal with a wavelength from 890-910 nm (infrared); LS2 32 can be configured to generate a second portion of the light signal with a wavelength from 600-700 nm (red), and LS3 36 can be configured to generate a third portion of the light signal with a wavelength from 810-880 nm. In this example, LS1 36, which is in the middle of each light delivery source cluster 26, can operate in the super-pulsed operating mode, while LS2 32 and LS3 36, which surround LS1, can each operate in the continuous operating mode or the pulsed operating mode. In other words, LS1 can be a super pulsed laser that creates an impulse of high intensity that emits for a billionth of a second in synchrony with LS2 (a red source, like a red LED or a red light) and/or LS3 (an infrared source, like an infrared LED or an infrared light). The synchronous combination can operate according to a pre-determined frequency corresponding to a frequency of a brain wave that the light signal is trying to emulate. Advantageously, the use of the super-pulsed laser (LS1) allows a desired peak power to be delivered for an ultrashort pulse with a minimized level of heat accumulated in the subject's head, skull, or brain (in other words, minimizes the photothermal effect).

Many configurations of each light delivery source cluster 26 are possible. Two examples of possible configurations are set forth, but countless other possibilities exist (including with other light sources), as long as there are one or more L1, one or more L2, one or more L3. One possible configuration of each light delivery source cluster 26 is a 1:1:1 configuration, with L1 (the super-pulsed laser) between L2 (the red source) and L3 (the infrared source). Another possible configuration of each light delivery source cluster 13 is a 1:3:3 configuration with L1 surrounded by three (or more) L2 and three (or more) L3. For example, in this configuration, L2 and L3 can alternate as they are arranged around L1 (e.g., L2 L3 L2 L3 L2 L3 surrounding L1). As another example, L2 and L3 can be grouped together around L1 (e.g., L2 L2 L2 L3 L3 L3). Although not expressly described, other example configurations are possible in the 1:3:3 light delivery source cluster 26. The light delivery source clusters 26 within the same light source device 14 can be configured identically, but need not have identical configurations. For example, a light source device 14 can have three light delivery source clusters, with one a 1:1:1 configuration and the other two 1:3:3 configurations.

Referring again to FIG. 1, the transcranial stimulation mechanism 16 can be configured to deliver the transcranial stimulation to the target area. For example, the transcranial stimulation mechanism 16 can deliver transcranial direct current electrical stimulation (tDCS), transcranial magnetic stimulation (tMS). To facilitate the transcranial delivery, the light source device 14 and/or the transcranial stimulation mechanism 16 (in some instances) can be shaped so that at least a portion of the light source device 14 and/or the transcranial stimulation mechanism 16 makes contact with a subject's head proximal to the defined target area of the brain.

The controller 12 can deliver inputs to the light source device 14 and the transcranial stimulation mechanism 16. The inputs can include factors related to a predetermined stimulation paradigm. In some instances, the controller 12 can include a processing unit that can be preprogrammed according to the stimulation paradigm. For example, the stimulation paradigm can include times for application of the different transcranial therapies, order of application of the different transcranial therapies, intensity of the transcranial stimulation, frequency of the light signal, etc. As an example, the controller can program a frequency of the light signal based on a target brain wave so that the light signal includes pulses at the frequency. For example, the frequency can be between 0 Hz and 80 Hz. As another example, the frequency can be between 5 Hz and 50 Hz. The controller 12 can be connected to the light source device 14 and the transcranial stimulation mechanism 16 to allow data transmission according to a wired connection and/or a wireless connection.

Figure 4:
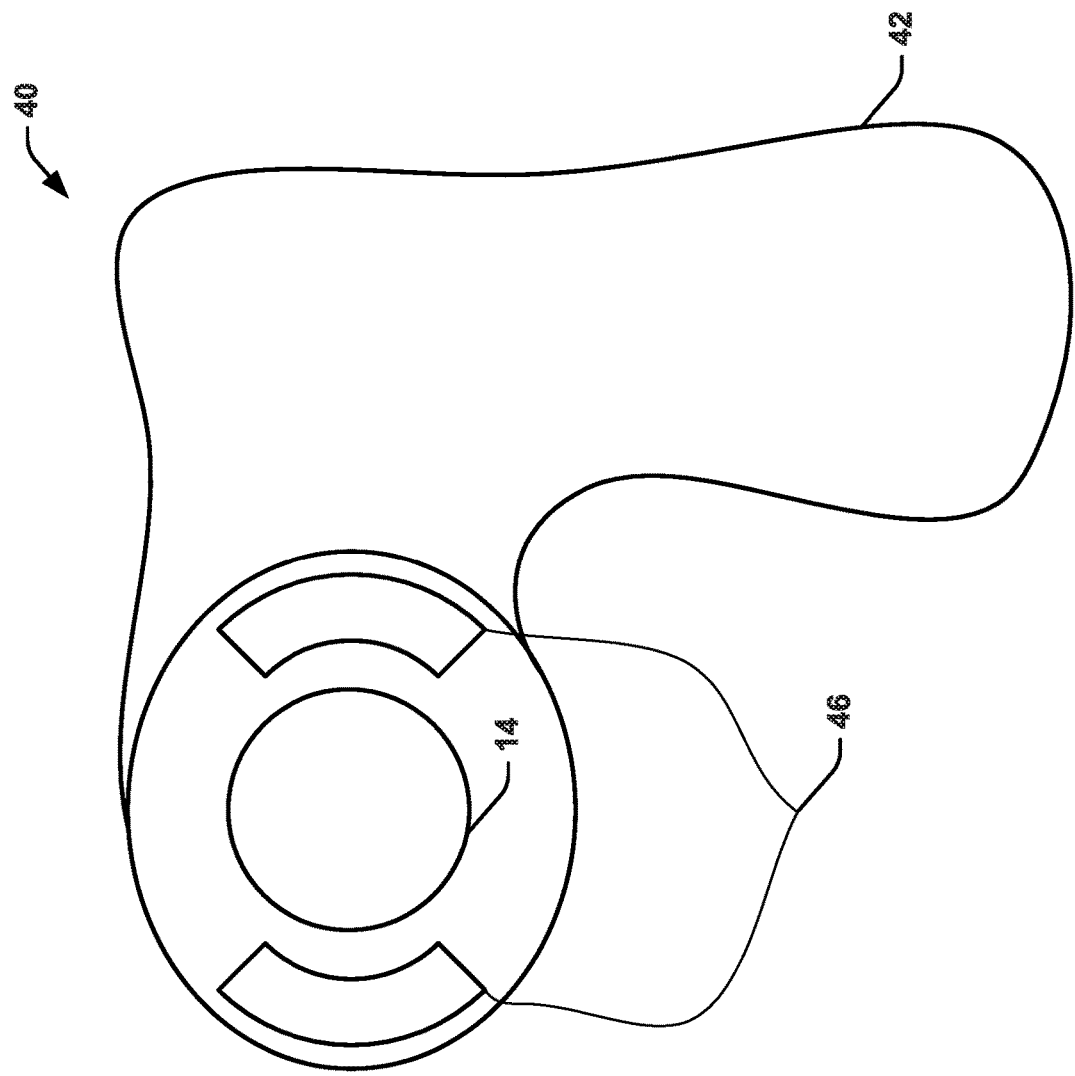
FIG. 4 is a diagram of an example device that can be used to implement the system of FIG. 1.

An example implementation 40 of the system 10 is shown in FIG. 4. The implementation 40 is a probe device that can include a device housing 42 that is made of a hard material (e.g., a plastic). The device housing 42 can include extra elements of the system 10, such as the power source and the controller 12. The device housing 42 include a portion configured to contact the subject's head proximal to the target area at a 90-degree angle to deliver the light signal and the stimulation. In this example, the stimulation can be magnetic stimulation delivered by two magnets 46 arranged on either side of the light source device 14 as described above. The magnets 46 can be permanent magnets to provide a static (or constant) magnetic field. Either individually or together, the magnets 46 can provide a constant magnetic field from 5 mT to 15 T that can deliver the tMS to the patient.

V. Methods

Another aspect of the present disclosure can include methods 50, 60 (FIGS. 5 and 6) that are used to restructure a neural pathway in the brain. The restructured neural pathway is created by applying a combination of transcranial therapies to an area of the brain to treat brain dysfunction. The methods 50, 60 can be executed by hardware—for example, at least a portion of the system 10 shown in FIG. 1 and described above.

The methods 50 and 60 are illustrated as process flow diagrams with flowchart illustrations. For purposes of simplicity, the methods 50 and 60 shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 50 and 60. Additionally, one or more elements that implement the methods 50 and 60, such as light source device 14, the transcranial stimulation mechanism 16, and/or the controller 12 of FIG. 1, may include a non-transitory memory and one or more processors that can facilitate the configuration and generation of the combination of transcranial therapies.

Figure 5:
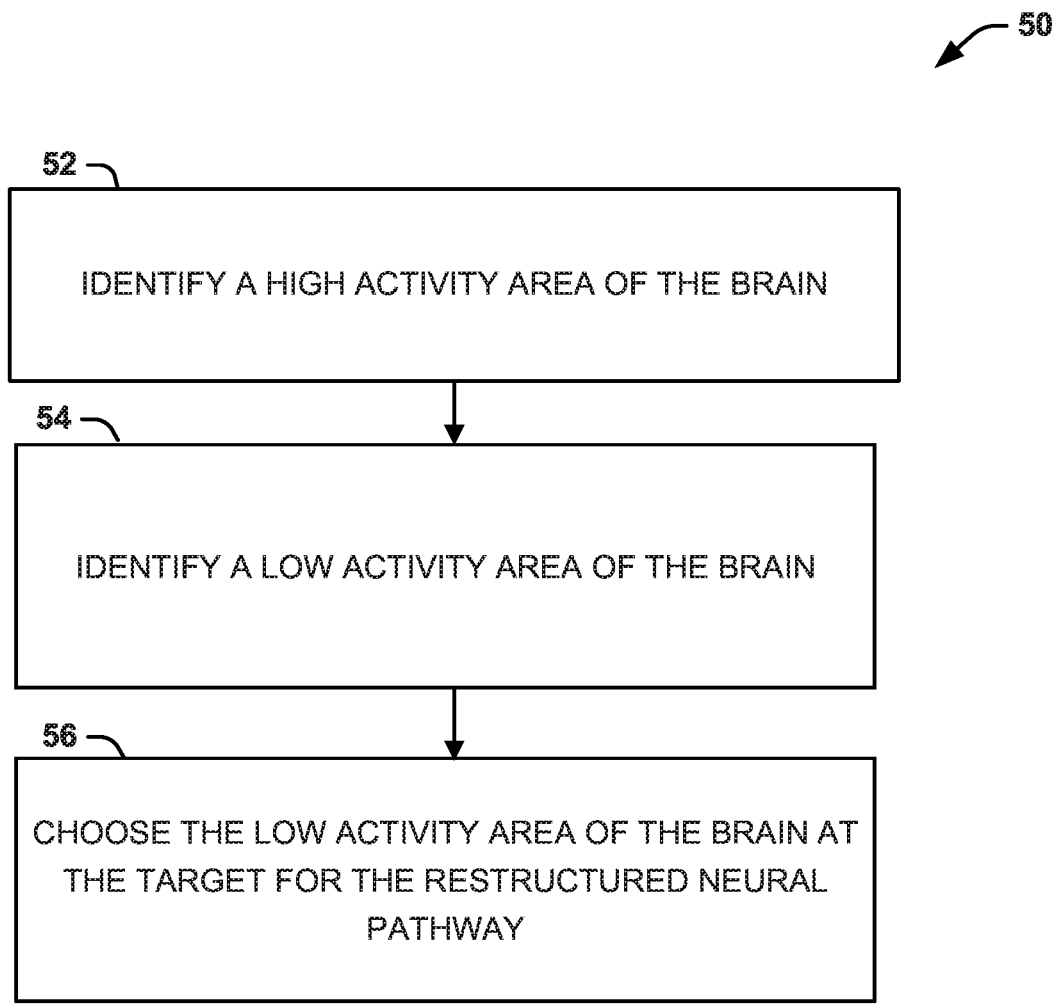
FIG. 5 is a process flow diagram of an example method for identifying high and low activity areas of the brain in accordance with another aspect of the present disclosure.

Referring now to FIG. 5, illustrated is a method 50 for identifying high and low activity areas of the brain. To identify these areas, a patient can undergo electroencephalogram (EEG) testing. For example, the EEG testing can record EEG data based on recordings collected by an 18-channel EEG recording device.

At step 52, a high activity area of the brain can be identified based on the EEG data. For example, the high activity area can be identified based on conduction patterns seen in the EEG data. The high activity area of the brain can indicate brain circuit asymmetry. The high activity area can exhibit hyperactivity causing the brain dysfunction associated with a neurological disorder. The neurological disorder can be, for example, autism, Alzheimer's disease, epilepsy, depression, anxiety, traumatic brain injury, or the like.

At step 54, a low activity area of the brain can be identified based on the EEG data. For example, the low activity area can be identified based on different conduction patterns seen in the EEG data. The low activity area of the brain does not exhibit hyperactivity, so that the low activity area of the brain is not exhibiting the dysfunction. For example, the high activity area of the brain and the low activity area of the brain may be identified based on conduction patterns shown in the EEG data.

At step 56, the low activity area of the brain can be chosen as the target for the restructured neural pathway. In other words, the low activity area of the brain can be chosen as the area of the brain requiring stimulation. Based on the simulation with type different types of stimulation (e.g., transcranial stimulation and transcranial photobiomodulation therapy (PBMT)), the neural pathway can be rerouted through the low activity area of the brain.

Figure 6:
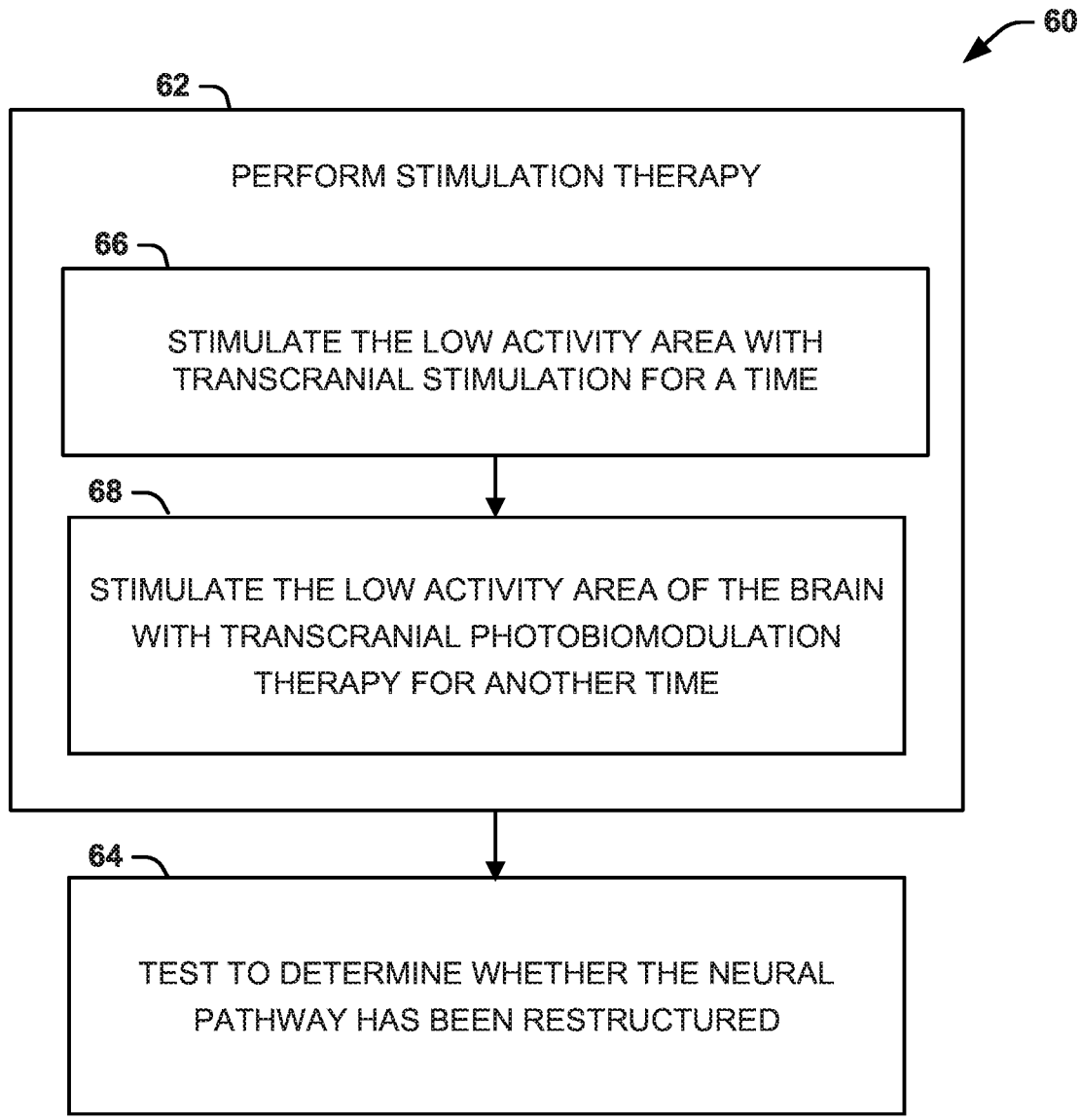
FIG. 6 is a process flow diagram of another example method for restructuring a neural pathway in the brain in accordance with a further aspect of the present disclosure.

FIG. 6 shows a method 60 for restructuring the neural pathway in the brain by rerouting the neural pathway away from the area of high activity in the brain and, instead, through the area of low activity in the brain. At step 62, stimulation therapy can be performed on the patient. After a time (e.g., a certain number of stimulation therapy sessions), at step 64, a test can be conducted to determine whether the neural pathway has been restructured. The test can be another EEG to reveal new conduction patterns. For example, an indication that the stimulation therapy has been effective would be if the high activity area showed less hyperactivity.

The stimulation of step 62 can include both steps 66 (transcranial stimulation) and 68 (transcranial photobiomodulation therapy (PBMT)). The stimulation can cause the brain to undergo neuroplasticity to form the desired neural pathway in response to application of the transcranial stimulation and transcranial PBMT with a light signal. In some instances, the transcranial stimulation and the light signal can be delivered sequentially (in any order). The stimulation can be conducted according to a dosage requirement (e.g., an intensity of the transcranial stimulation, a frequency of the light signal, a time of application for either of the transcranial stimulation or the light signal, or the like). A determination of the dosage requirements can be made based on the certain neurological disorder or a characteristic of the certain neurological disorder.

At step 66, the low activity area of the brain can be stimulated with transcranial stimulation for a time. The transcranial stimulation can be delivered at an intensity. For example, the transcranial stimulation can be transcranial direct current stimulation (tDCS), transcranial magnetic stimulation (tMS), or the like. At step 68, the low activity area of the brain can be stimulated with a light signal of transcranial PBMT for another time. The light signal can include a series of pulses having a frequency matched to a target brain wave. In some instances, the frequency can be between 0 Hz and 80 Hz. In other instances, the frequency can be between 5 Hz and 50 Hz. However, the frequency can be any value that matches a particular brain wave associated with the certain neurological disorder.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The following is claimed:

1. A method comprising:
    delivering a transcranial stimulation at an intensity and for a time to a low activity area of a brain of a patient that does not exhibit hyperactivity identified based on electroencephalogram (EEG) data, wherein the low activity area of the brain is a target for a restructured neural pathway away from a high activity area of the brain that exhibits hyperactivity; and
    delivering a light signal in a transcranial manner to the low activity area of the brain for a second time in sequence with the transcranial stimulation, wherein the light signal comprises a series of pulses having a frequency matched to a target brain wave to facilitate the restructuring of the neural pathway away from the high activity area of the brain;
    wherein the brain undergoes neuroplasticity to form the restructured neural pathway in response to the transcranial stimulation and the light signal,
    wherein the transcranial stimulation and the light signal are delivered by a same device, wherein the same device comprises a magnetic source or an electrical source to provide the transcranial stimulation and a light source to provide the light signal, and
    wherein the light source comprises a cluster of light delivery sources, the cluster of light delivery sources comprises:
    a first light delivery source configured to generate a first portion of the light signal in a super-pulsed operating mode;
    a second light delivery source configured to generate a second portion of the light signal in a pulsed operating mode or a continuous operating mode; and
    a third delivery light source configured to generate a third portion of the light signal in the pulsed operating mode or the continuous operating mode.

2. The method of claim 1, wherein forming the restructured neural pathway treats a brain circuit asymmetry characteristic of a neurological disorder.

3. The method of claim 2, wherein the neurological disorder is autism, Alzheimer's disease, epilepsy, depression, anxiety, or traumatic brain injury.

4. The method of claim 1, wherein the transcranial stimulation comprises transcranial direct current stimulation (tDCs) or transcranial magnetic stimulation (tMS).

5. The method of claim 1, wherein the frequency is from 0 Hz to 80 Hz.

6. The method of claim 1, wherein the frequency is from 5 Hz to 50 Hz.

7. The method of claim 1, further comprising determining the low activity area of the brain based on the EEG data.

8. The method of claim 7, wherein the determining further comprises:
   identifying the high activity area from the EEG data;
   identifying the low activity area from the EEG data; and
   choosing the low activity area as the low activity area of the brain.

9. The method of claim 8, wherein the high activity area indicates brain circuitry asymmetry.

10. The method of claim 8, wherein the high activity area and the low activity area are identified based on conduction patterns shown in the EEG data.

11. The method of claim 7, wherein the EEG data is collected by an 18-channel EEG recording device.

12. A system comprising:
   a transcranial stimulation mechanism to deliver a transcranial stimulation at an intensity and for a time to a low activity area of a brain of a patient that does not exhibit hyperactivity identified based on electroencephalogram (EEG) data wherein the low activity area of the brain is a target for a restructured neural pathway away from a high activity area of the brain that exhibits hyperactivity;
   a light source device to deliver a light signal in a transcranial manner to the low activity area of the brain for a second time in sequence with the transcranial stimulation, wherein the light signal comprises a series of pulses having a frequency matched to a target brain wave to facilitate the restructuring of the neural pathway away from the high activity area of the brain,
   wherein the light source device comprises a cluster of light delivery sources, the cluster of light delivery sources comprises:
   a first light delivery source configured to generate a first portion of the light signal in a super-pulsed operating mode;
   a second light delivery source configured to generate a second portion of the light signal in a pulsed operating mode or a continuous operating mode; and
   a third light delivery light source configured to generate a third portion of the light in the pulsed operating mode or the continuous operating mode;
   a processing unit preprogrammed to apply the transcranial stimulation for the time in sequence with the light signal for the second time; and
   a power source to provide power to at least the processing unit.

13. The system of claim 12, wherein the frequency is from 5 Hz to 50 Hz.

14. The system of claim 12, wherein the light signal has a wavelength from 600 nm to 1100 nm.

15. The system of claim 12, wherein the transcranial stimulation mechanism comprises a permanent magnet that provides a constant magnetic field from 5 mT to 5 T.

* * * * *